US011118285B2

(12) United States Patent
Muramatsu et al.

(10) Patent No.: US 11,118,285 B2
(45) Date of Patent: Sep. 14, 2021

(54) METHOD OF EVALUATING CLEANLINESS, METHOD OF DETERMINING CLEANING CONDITION, AND METHOD OF MANUFACTURING SILICON WAFER

(71) Applicant: SUMCO CORPORATION, Tokyo (JP)

(72) Inventors: Takashi Muramatsu, Saga (JP); Hirokazu Kato, Nagasaki (JP)

(73) Assignee: SUMCO CORPORATION, Tokyo (JP)

( * ) Notice: Subject to any disclaimer, the term of this patent is extended or adjusted under 35 U.S.C. 154(b) by 0 days.

(21) Appl. No.: 16/087,879

(22) PCT Filed: Feb. 28, 2017

(86) PCT No.: PCT/JP2017/007749
§ 371 (c)(1),
(2) Date: Sep. 24, 2018

(87) PCT Pub. No.: WO2017/169458
PCT Pub. Date: Oct. 5, 2017

(65) Prior Publication Data
US 2019/0106810 A1    Apr. 11, 2019

(30) Foreign Application Priority Data
Mar. 28, 2016  (JP) .............................. JP2016-064071

(51) Int. Cl.
| C30B 29/06 | (2006.01) |
| G01N 27/62 | (2021.01) |
| H01L 21/304 | (2006.01) |
| H01L 21/02 | (2006.01) |
| C30B 29/36 | (2006.01) |
| C30B 23/02 | (2006.01) |
| G01N 33/00 | (2006.01) |

(52) U.S. Cl.
CPC ............. *C30B 29/06* (2013.01); *G01N 27/62* (2013.01); *H01L 21/02529* (2013.01); *H01L 21/304* (2013.01); *C30B 23/02* (2013.01); *C30B 29/36* (2013.01); *G01N 2033/0095* (2013.01)

(58) Field of Classification Search
CPC ....... C07C 39/08; C07C 37/685; C07C 37/86; C30B 23/02; C30B 29/06; G01N 2033/0095; G01N 27/62; H01L 21/02529; H01L 21/304
See application file for complete search history.

(56) References Cited

U.S. PATENT DOCUMENTS

2006/0157448 A1    7/2006 Magni et al.
2006/0234058 A1*   10/2006 Ohmi ..................... C30B 29/36
                                                            428/409

FOREIGN PATENT DOCUMENTS

| CN | 102079523 A | 6/2011 |
| CN | 102602935 B | 3/2014 |
| CN | 103681246 A | 3/2014 |
| CN | 104280382 A | 1/2015 |
| JP | 08078375 A | * 3/1996 |
| JP | H10-74481 A | 3/1998 |
| JP | 2000-169233 A | 6/2000 |
| JP | 2000-332072 A | 11/2000 |
| JP | 2000-335992 A | 12/2000 |
| JP | 2002-040009 A | 2/2002 |
| JP | 2010-004073 A | 1/2010 |
| JP | 2012-132779 A | 7/2012 |
| JP | 2012132779 A | * 7/2012 |
| TW | 2013-18979 A | 5/2013 |

OTHER PUBLICATIONS

Official Action issued in Taiwanese Patent Application No. 106106372, dated Dec. 12, 2017, along with an english translation thereof.
International Search Report issued in the International Bureau of WIPO Patent Application No. PCT/JP2017/007749, dated May 30, 2017, along with an English translation thereof.
International Preliminary Report on Patentability issued in thee International Bureau of WIPO Patent Application No. PCT/JP2017/007749, dated Oct. 11, 2018, along with an English translation thereof.
Office Action for KR App. No. 10-2018-7026228, dated May 12, 2020 (w/ machine translation).
Office Action issued in corresponding Korean patent application No. 10-2018-7026228 dated Jan. 15, 2020; along with English-language translation thereof.
Office Action for CN App. No. 201780016301.5, dated Sep. 2, 2020 (w/ translation).
Office Action for CN App. No. 201/80016301.5, dated Apr. 16, 2021 (w/ translation).

* cited by examiner

*Primary Examiner* — Hua Qi

(74) *Attorney, Agent, or Firm* — Greenblum & Bernstein, P.L.C.

(57) ABSTRACT

Provided is a method of evaluating cleanliness of a member having a silicon carbide surface, the method including bringing the silicon carbide surface into contact with a mixed acid of hydrofluoric acid, hydrochloric acid and nitric acid; concentrating the mixed acid brought into contact with the silicon carbide surface by heating; subjecting a sample solution obtained by diluting a concentrated liquid obtained by the concentration to quantitative analysis of metal components by Inductively Coupled Plasma-Mass Spectrometry; and evaluating cleanliness of the member having a silicon carbide surface on the basis of a quantitative result of metal components obtained by the quantitative analysis.

9 Claims, No Drawings

METHOD OF EVALUATING CLEANLINESS, METHOD OF DETERMINING CLEANING CONDITION, AND METHOD OF MANUFACTURING SILICON WAFER

CROSS-REFERENCE TO RELATED APPLICATIONS

This application claims the benefit of priority to Japanese Patent Application No. 2016-064071 filed on Mar. 28, 2016, which is expressly incorporated herein by reference in its entirety.

TECHNICAL FIELD

The present invention relates to a method of evaluating cleanliness, a method of determining a cleaning condition, and a method of manufacturing a silicon wafer. Specifically, the present invention relates to a method of evaluating cleanliness of a member having a silicon carbide surface, a method of determining a cleaning condition of a member having a silicon carbide surface, and a method of manufacturing a silicon wafer.

BACKGROUND ART

It is generally said that silicon carbide (SiC) is a material excellent in heat resistance, chemical durability and the like. Accordingly, silicon carbide is widely used as a material constituting various members in various types of technical fields. As an example, in a field of manufacturing a silicon wafer (hereinafter, also referred to as a "wafer"), coating, with silicon carbide, a surface of an internal member (such as a heat-shielding member) of a lifting machine to be used in manufacturing a single crystal silicon ingot that is sliced to give a silicon wafer or a surface of a member for placing a silicon wafer (such as a susceptor or a wafer boat) in heat treatment; constituting the whole member from silicon carbide; or the like is being performed. In the following, a member whose surface is at least partially made of silicon carbide, that is, a member having at least partially a silicon carbide surface (SiC surface) is described as a "silicon carbide-based member."

With respect to a silicon carbide-based member, a silicon carbide-based member is cleaned for the reduction of metal contamination from the silicon carbide-based member (refer to, for example, Japanese Unexamined Patent Publication (KOKAI) No. 2010-4073 and Japanese Unexamined Patent Publication (KOKAI) No. 2000-169233, which are expressly incorporated herein by reference in their entirety).

SUMMARY OF THE INVENTION

For example, with respect to a silicon wafer, metal contamination of a silicon wafer is required to be lowered since the contamination affects properties of a device to be produced using the wafer. A cause of the metal contamination of a silicon wafer includes the fact that, as a result of metal contamination of a member coming into contact with a wafer during a manufacturing process of a single crystal silicon ingot or a silicon wafer, the metal element diffuses from the member into the atmosphere and is incorporated into the single crystal silicon ingot or the silicon wafer, or a silicon wafer is metal-contaminated as a consequence of contact of the wafer with the member. Accordingly, in a process for manufacturing a silicon wafer including a process using a silicon carbide-based member, it is desirable to clean a silicon carbide-based member to thereby lower metal contamination of the silicon carbide-based member. Furthermore, it is more desirable to evaluate cleanliness as to whether or not a silicon carbide-based member is in a state where metal contamination has sufficiently been reduced and cleaned by the cleaning, and to examine the change or the like of a cleaning condition if the cleanliness is insufficient. A method of evaluating cleanliness of a silicon carbide-based member for this purpose requires the capability of highly accurately evaluating metal contamination of a silicon carbide-based member.

An aspect of the present invention provides for a means for highly accurately evaluating metal contamination of a silicon carbide-based member.

An aspect of the present invention relates to a method of evaluating cleanliness of a member (silicon carbide-based member) having a silicon carbide surface, the method including:

bringing the silicon carbide surface into contact with a mixed acid of hydrofluoric acid, hydrochloric acid and nitric acid;

concentrating the mixed acid brought into contact with the silicon carbide surface by heating;

subjecting a sample solution obtained by diluting a concentrated liquid obtained by the concentration to quantitative analysis of metal components by Inductively Coupled Plasma-Mass Spectrometry (ICP-MS); and evaluating cleanliness of the member having a silicon carbide surface on the basis of a quantitative result of metal components obtained by the quantitative analysis.

In an embodiment, in the mixed acid, a concentration of hydrofluoric acid ranges from 5 to 15 mass %, a concentration of hydrochloric acid ranges from 5 to 15 mass %, and a concentration of nitric acid ranges from 5 to 15 mass %.

In an embodiment, the sample solution is prepared by diluting the concentrated liquid obtained by the concentration through the addition of hydrofluoric acid and hydrogen peroxide.

In an embodiment, the member having a silicon carbide surface is a member for manufacturing a silicon wafer.

In an embodiment, the member for manufacturing a silicon wafer is a susceptor.

A further aspect of the present invention relates to a method of determining a cleaning condition of a member having a silicon carbide surface, the method including:

cleaning a silicon carbide surface of a member having a silicon carbide surface under a candidate cleaning condition;

evaluating cleanliness of the member having a silicon carbide surface after the cleaning by the above method of evaluating cleanliness; and determining a candidate cleaning condition under which the cleanliness has been determined to be within an allowable level as a result of the evaluation, as a cleaning condition of a member having a silicon carbide surface in an actual manufacturing process of a silicon wafer.

A further aspect of the present invention relates to a method of manufacturing a silicon wafer, including:

determining a cleaning condition by the above method of determining a cleaning condition;

cleaning a member for manufacturing a silicon wafer having a silicon carbide surface under the determined condition; and manufacturing a silicon wafer through a manufacturing process including a process using the cleaned member for manufacturing a silicon wafer.

A further aspect of the present invention relates to a method of manufacturing a silicon wafer, including:

evaluating cleanliness of a member for manufacturing a silicon wafer having a silicon carbide surface by the above method of evaluating cleanliness; and manufacturing a silicon wafer through a manufacturing process including a process using a member for manufacturing a silicon wafer, whose cleanliness has been determined to be within an allowable level as a result of the evaluation.

According to an aspect of the present invention, it becomes possible to highly accurately evaluate metal contamination of a member having a silicon carbide surface (silicon carbide-based member).

DESCRIPTION OF EMBODIMENTS

[Method of Evaluating Cleanliness]

An aspect of the present invention relates to a method of evaluating cleanliness of a member having a silicon carbide surface (silicon carbide-based member), the method including: bringing the silicon carbide surface into contact with a mixed acid of hydrofluoric acid, hydrochloric acid and nitric acid; concentrating, by heating, the mixed acid brought into contact with the silicon carbide surface; subjecting a sample solution obtained by diluting a concentrated liquid obtained by the concentration to quantitative analysis of metal components by Inductively Coupled Plasma-Mass Spectrometry (ICP-MS); and evaluating cleanliness of the member having a silicon carbide surface on the basis of a quantitative result of metal components obtained by the quantitative analysis, (hereinafter, the above method is also referred to simply as a "method of evaluating cleanliness").

In the present invention and present description, "cleanliness" means a degree of metal contamination. The method of evaluating cleanliness according to an aspect of the present invention makes it possible to highly accurately evaluate cleanliness of a silicon carbide-based member. The present inventors presume that the facts that: the mixed acid can recover, at a high recovery rate, metal components from a silicon carbide-based surface; the mixed acid having recovered, at a high recovery rate, metal components from the silicon carbide-based surface is concentrated by heating; and quantitative analysis is performed with ICP-MS that is a highly sensitive analysis apparatus, contributes to the reason why high-accurate evaluation becomes possible. However, the above is presumption, and does not limit the present invention at all.

Hereinafter, the method of evaluating cleanliness will be explained in more detail.

<Evaluation-Target Member>

An evaluation target of the method of evaluating cleanliness is a member having a silicon carbide surface (silicon carbide-based member). The silicon carbide surface means a surface constituted of silicon carbide. In a member having a silicon carbide surface, the whole or a part of the surface of the member is a silicon carbide surface. The member having a silicon carbide surface is: in an embodiment, a member whose surface is at least partially, that is, partially or wholly covered with silicon carbide; in another embodiment, a member that is wholly made of silicon carbide; and, furthermore, in other embodiments, a member that is partially made of silicon carbide and the part composed of silicon carbide is exposed to a part of the surface of the member. In a silicon carbide-based member having silicon carbide as a covering layer that covers at least a part of a member, a thickness of the covering layer is not particularly limited. In addition, a size and a shape of a silicon carbide-based member that is an evaluation target are also not particularly limited.

For example, when a manufacturing process of a silicon wafer is taken as an example, a silicon carbide-based member is widely used as a member for manufacturing a silicon wafer. Examples of silicon carbide-based members for manufacturing a silicon wafer can include: an internal member (such as a heat-shielding member) of a lifting machine to be used in manufacturing a single crystal silicon ingot; a susceptor (a wafer-placing member); a lift pin of a susceptor; a boat in a heat treatment furnace or CVD (Chemical Vapor Deposit) furnace; and the like, and evaluation of cleanliness of these various members can be performed by the method of evaluating cleanliness according to an aspect of the present invention. However, evaluation-target members in the method of evaluating cleanliness according to an aspect of the present invention are not limited to members for manufacturing a silicon wafer. If these are members having a silicon carbide surface (silicon carbide-based members), it is possible to set, as evaluation targets, silicon carbide-based members to be used not only in a field of manufacturing a silicon wafer, but also in various fields.

According to the examination by the present inventors, recovery of metal components from a silicon carbide surface is more difficult than recovery of metal components from a silicon wafer surface. With respect to the reason thereof, although the following is only presumption, the present inventors presume that one cause is a rougher surface of a silicon carbide than a surface of a silicon wafer. For example, SRc (average peak height of roughness curved surface) of a silicon carbide surface can be equal to or higher than 1.00 μm (for example, approximately 1.00 to 10.00 μm), and SPc (average peak height of cross-section curved surface) thereof can be equal to or higher than 1.00 μm (for example, approximately 1.00 to 10.00 μm). Here, the SRc is a value to be measured by the method specified in JIS B 0601-2001, and the SPc is a value to be measured by the method specified in ISO 25178.

<Mixed Acid>

In the method of evaluating cleanliness, the silicon carbide surface of a silicon carbide-based member being an evaluation target is brought into contact with a mixed acid of hydrofluoric acid (HF), hydrochloric acid (HCl) and nitric acid ($HNO_3$). In the following, the mixed acid is also described as a "recovery liquid." The recovery liquid containing the above three kinds of acids can recover metal components adhering to a silicon carbide surface, that is, can incorporate metal components adhering to a silicon carbide surface into the recovery liquid, at a high recovery rate. This point was newly found out as the result of keen examinations by the present inventors.

As to concentrations of the three kinds of acids contained in the mixed acid, the concentration of hydrofluoric acid ranges preferably from 5 to 15 mass % and more preferably from 5 to 10 mass %, the concentration of hydrochloric acid ranges preferably from 5 to 15 mass % and more preferably from 10 to 15 mass %, and the concentration of nitric acid ranges preferably from 5 to 15 mass % and more preferably from 10 to 15 mass %. The mixed acid can preferably be an aqueous solution of the above three kinds of acids.

Contact of the mixed acid with a silicon carbide surface can be performed by a known contact method such as a method of immersing a member having a silicon carbide surface (silicon carbide-based member) into the mixed acid, a method of scanning the mixed acid onto a silicon carbide surface, or the like. An amount of the mixed acid to be used here is not particularly limited, and the mixed acid having an amount suitable for the contact method may be used. Furthermore, contact of the mixed acid with a silicon carbide surface can be performed, for example, under the atmospheric pressure and at room temperature (for example, approximately 15 to 25° C.), and the mixed acid can be used without temperature control (heating or cooling).

<Preparation of Sample Solution>

As a consequence of contacting a silicon carbide surface with the mixed acid as described above, metal components adhering to a silicon carbide surface can be recovered into the mixed acid. However, it is considered that, when the mixed acid having recovered metal components is directly introduced into ICP-MS, interference with a mass number of an evaluation-target metal is induced, whereby decrease in quantitative accuracy, sensitivity reduction, apparatus deterioration, and the like are caused. Accordingly, in the above method of evaluating cleanliness, a sample solution having been prepared as follows is subjected to quantitative analysis of a metal component by ICP-MS. The present inventors consider that this point also contributes to allowing high-accurate evaluation.

(Heating Concentration)

For preparing a sample solution, first, the mixed acid brought into contact with a silicon carbide surface is heated for concentration. Heating can be performed by a known method for concentrating solution by heating such as a method of heating, on a hot plate, a vessel (such as a beaker) containing the mixed acid brought into contact with a silicon carbide surface. Concentration by heating is preferably performed so as to allow liquid to remain without complete drying and solidification. The amount of liquid allowed to remain can be set to, for example, approximately 10 to 50 µL. Among metal components, there is a metal component that volatilizes due to complete drying and solidification, and thus it is preferable to allow liquid to remain without performing complete drying and solidification in order to make quantitative determination of such metal components possible. A liquid amount of the mixed acid (mixed acid amount) before concentration is, for example, approximately 5000 to 1000 µL, but, as described above, a mixed acid amount to be brought into contact with a silicon carbide surface is not particularly limited. Therefore, the amount may be larger or smaller than the above range.

(Dilution)

After that, a concentrated liquid obtained by the concentration is diluted, whereby a sample solution to be introduced into ICP-MS is prepared. Various kinds of dilute acids known as a dilute acid capable of being introduced into ICP-MS can be used for the dilution. Here, "dilute acid" means an acid solution (for example, an aqueous solution) in which a concentration of a contained acid (in a case where plural acids are contained, each concentration of each of these acids) is less than 3 mass %. Examples of preferable dilute acids can include a mixed acid of hydrochloric acid and hydrogen peroxide ($HCl/H_2O_2$), dilute nitric acid (dilute $HNO_3$), and the like. Here, the concentration of each acid can be, for example, approximately 1 to 3 mass %. A dilution ratio may be suitably determined by the amount of a concentrated liquid before dilution. As an example, on a volume basis, the dilution ratio can be set to approximately 20 to 100 times relative to an amount of a concentrated liquid before the dilution. The dilution ratio here means that, for example, a dilution ratio is 20 times when the amount of liquid obtained by dilution is 20 times the amount of a concentrated liquid before the dilution, on a volume basis.

<Quantitative Analysis>

The sample solution obtained as described above is subjected to quantitative analysis of metal components by ICP-MS. ICP-MS is an analysis method that can quantitatively analyze metal components with high sensitivity. It becomes possible to highly accurately evaluate cleanliness by subjecting the sample solution to quantitative analysis by ICP-MS. Usually, in ICP-MS, a sample solution is gasified or aerosolized with a nebulizer, which is then introduced into argon plasma generated by high-frequency power applied with an inductively-coupled coil. The sample is heated to approximately 6000 to 7000 K in atmospheric pressure plasma, and each element is atomized, and furthermore, ionized with an efficiency of usually equal to or higher than 90%. Ions pass through a skimmer (interface), are then energy-focused by an ion lens part, and subsequently are introduced into a mass spectrometer maintained at a high-vacuum state of, for example, $<10^{-6}$ Pa to thereby be subjected to mass analysis. Accordingly, metal components in the sample solution can be quantified. Quantitative analysis of metal components by ICP-MS can be performed using a commercially available ICP-MS or an ICP-MS having a known configuration. ICP-MS can quantitatively analyze various metal components. Specific examples of metal components (metal elements) to be quantitatively analyzed can include Na, Al, Cr, Fe, Ni, Cu, Mo, W, Ti, Nb, Ta, K, Ca, Zn, Co, Mg, Mn, Li, Sr, Ag, Pb, V, Ba and the like.

The larger amount of metal components contained in the sample solution means that the silicon carbide surface being an evaluation target was more contaminated with the metal components, namely, had lower cleanliness. Accordingly, cleanliness of a silicon carbide surface being an evaluation target can be evaluated on the basis of a quantitative result by ICP-MS. The evaluation of cleanliness may be given as a degree of contamination by a specified metal component, or be given on the basis of the sum of contamination amounts by metal components of equal to or more than two kinds.

[Method of Determining Cleaning Condition]

The method of evaluating cleanliness as described above can be used, in an embodiment, for determining a cleaning condition of a member having a silicon carbide surface.

That is, an aspect of the present invention relates to a method of determining a cleaning condition of a member having a silicon carbide surface, the method including:

cleaning a silicon carbide surface of a member having a silicon carbide surface under a candidate cleaning condition;

evaluating cleanliness of the member having a silicon carbide surface after the cleaning by the above method of evaluating cleanliness; and, determining a candidate cleaning condition under which the cleanliness has been determined to be within an allowable level as the result of the evaluation, as a cleaning condition of a member having a silicon carbide surface in an actual manufacturing process of a silicon wafer. According to the above method of evaluating cleanliness, cleanliness of a member having a silicon carbide surface (silicon carbide-based member) can be highly accurately evaluated. The above method of determining a cleaning condition makes it possible, by determining, on the basis of the evaluation result, whether or not a candidate cleaning condition is suitable as a cleaning condition in an actual manufacturing process, to use a silicon carbide-based member considered to give high cleanliness by the cleaning in the actual manufacturing process. In addition, accordingly, metal contamination of a silicon wafer by a silicon carbide-based member can be suppressed in the actual manufacturing process.

Examples of cleaning conditions of a silicon carbide-based member can include a composition of a cleaning liquid, cleaning time, number of cleaning times, and the like. In a case where an evaluation result (cleanliness) obtained through evaluation of a silicon carbide-based member cleaned under a certain candidate cleaning condition, by the above method of evaluating cleanliness, is within an allowable level, the candidate cleaning condition can be determined as a cleaning condition of a silicon carbide-based member in an actual manufacturing process of a silicon wafer. The allowable level here is not particularly limited, and can be determined on the basis of cleanliness required for a silicon wafer in accordance with the intended use or the like of the silicon wafer. On the other hand, in a case where an evaluation result (cleanliness) obtained through evaluation of a silicon carbide-based member cleaned under a certain candidate cleaning condition, by the above method of evaluating cleanliness, exceeds an allowable level, the cleaning condition can be determined not to be applicable as a cleaning condition in an actual manufacturing process. In this case, it is also possible to modify the cleaning condition and determine a new candidate cleaning condition, and to perform evaluation with respect to the candidate cleaning condition. Furthermore, it is also possible to determine a cleaning condition of a silicon carbide-based member in an actual manufacturing process of a silicon wafer, by repeating determination and evaluation of such a new candidate cleaning condition.

Examples of silicon carbide-based members being cleaning targets can include various members exemplified above as members for manufacturing a silicon wafer. Furthermore, examples of silicon wafers to be manufactured in an actual manufacturing process can include, in addition to a so-called bare wafer, various silicon wafers such as a silicon epitaxial wafer having an epitaxial layer on a silicon substrate and a silicon wafer having a thermal oxide film as an outermost layer. Manufacturing processes of these silicon wafers are known.

[Method of Manufacturing Silicon Wafer]

A further aspect of the present invention relates to a method of manufacturing a silicon wafer, including:

determining a cleaning condition by the above method of determining a cleaning condition;

cleaning a member for manufacturing a silicon wafer having a silicon carbide surface under the determined cleaning condition; and manufacturing a silicon wafer through a manufacturing process including a process using the cleaned member for manufacturing a silicon wafer. (Hereinafter, the above method is referred to as a "manufacturing method 1.")

A further aspect of the present invention relates to a method of manufacturing a silicon wafer, including:

evaluating cleanliness of a member for manufacturing a silicon wafer having a silicon carbide surface, by the above method of evaluating cleanliness; and manufacturing a silicon wafer through a manufacturing process including a process using a member for manufacturing a silicon wafer, whose cleanliness has been determined to be within an allowable level as a result of the evaluation. (Hereinafter, the above method is referred to as a "manufacturing method 2.")

According to the manufacturing method 1, it is possible to manufacture a silicon wafer by the use of a silicon carbide-based member (member for manufacturing a silicon wafer) cleaned under a cleaning condition determined by the above method of determining a cleaning condition. The cleaning condition determined by the above method of determining a cleaning condition is a cleaning condition under which the capability of providing a silicon carbide-based member having a high cleanliness by the cleaning has been confirmed. As a consequence of using a silicon carbide-based member cleaned under the cleaning condition, it becomes possible to manufacture a silicon wafer with reduced metal contamination.

According to the manufacturing method 2, it is possible to manufacture a silicon wafer by the use of a silicon carbide-based member (member for manufacturing a silicon wafer) whose cleanliness has been confirmed as being high by the above method of evaluating cleanliness. Accordingly, it becomes possible to manufacture a silicon wafer with reduced metal contamination. An allowable level in the manufacturing method 2 is also not particularly limited, and can be determined on the basis of cleanliness required for a silicon wafer in accordance with the intended use of the silicon wafer.

Examples of members for manufacturing a silicon wafer in the manufacturing method 1 and the manufacturing method 2 can include various members exemplified above as members for manufacturing a silicon wafer. Examples of processes using the member can include various heat treatments such as a heat treatment for forming an epitaxial layer (vapor phase growth). In the heat treatment, a silicon wafer is placed on, for example, a member for manufacturing a silicon wafer (such as a susceptor and various kinds of boats as described above), and, at this time, the silicon wafer comes into contact with the member for manufacturing a silicon wafer. In addition, a lift pin of a susceptor comes into contact with a surface of a silicon wafer when it lifts the silicon wafer placed on the susceptor. Here, when the member for manufacturing a silicon wafer is metal-contaminated, the metal component adheres to the silicon wafer to thereby contaminate the silicon wafer. In addition, as a consequence of diffusion of an adhering metal component into the inside of the silicon wafer due to a heat treatment, the silicon wafer may also be metal-contaminated. In the manufacturing method 1 and the manufacturing method 2, for example, it is possible to reduce metal contamination of a silicon wafer which is generated in this way. As described above, a manufacturing process of a silicon wafer is known. In the manufacturing method 1 and the manufacturing method 2, a silicon wafer can be manufactured by a known manufacturing process.

EXAMPLES

Hereinafter, the present invention will be further explained on the basis of Examples. However, the present invention is not limited to embodiments shown in Examples. "%" described below means "mass %." The following processes and evaluations were performed under the atmospheric pressure and at room temperature (approximately 15 to 25° C.) and the mixed acid was used without temperature control (heating or cooling) unless otherwise noted.

1. Contamination of Silicon Carbide-Based Member with Metal Having Known Concentration A susceptor of a commercially available vapor-phase growth apparatus was subjected to a contamination treatment with a metal having a known concentration. The susceptor is a susceptor in which the whole surface of a carbon base material is covered with silicon carbide. The metal contamination treatment was performed by dropping a liquid containing a metal component having a known concentration onto a surface of the susceptor, and then by drying the liquid.

For the purpose of the following evaluations, plural susceptors subjected to a contamination treatment with a metal having a known concentration were prepared in the same way.

2. Recovery of metal component by contact of silicon carbide surface with mixed acid As a consequence of scanning (contacting) about 5000 to 10000 μL, of various kinds of mixed acids on the silicon wafer-placing surface (silicon carbide surface) of the susceptor subjected to the contamination treatment with a metal having a known concentration, a metal component adhering to the placing surface was recovered with a mixed acid. Mixed acids (recovery liquids) used were as follows:

mixed acid of hydrofluoric acid and nitric acid (HF (2%)/$HNO_3$ (2%))

[Comparative Example]

mixed acid of hydrofluoric acid, hydrochloric acid and hydrogen peroxide (HF (4%)/HCl (3%)/$H_2O_2$ (3%)) [Comparative Example], and mixed acid of hydrofluoric acid, hydrochloric acid and nitric acid (HF (8%)/HCl (12%)/$HNO_3$ (14%)) [Example].

Each of the mixed acids is an aqueous solution containing the acids as acid components and containing each acid in the concentration.

3. Concentration by Heating and Dilution of Recovered Liquid

The mixed acid (the recovery liquid) brought into contact with the silicon wafer-placing surface (silicon carbide surface) of the susceptor in the 2. was put in a beaker and was then heated on a hot plate (set temperature: 300° C.) to thereby be concentrated to a liquid amount of about 30 μL. A mixed acid of hydrofluoric acid and hydrogen peroxide (aqueous solution of hydrofluoric acid concentration 2% and hydrogen peroxide concentration 2%) was added to a beaker containing the concentrated liquid obtained by the concentration, and the liquid amount of the resultant diluted liquid was 1000 μL.

4. Quantitative Analysis of Metal Components by ICP-MS (1)

A sample solution obtained by the dilution in the 3 was introduced into an Inductively-Coupled Plasma Mass Spectrometer (ICP-MS) and quantitative analysis of metal components was performed.

The contamination amount of a known concentration in the 1. was set to 100%, and each metal component amount determined quantitatively by ICP-MS relative to the contamination amount of a known concentration was calculated as a recovery rate.

Table 1 below shows quantitative analysis results (recovery rates, average of recovery rates, and variation) obtained by performing the processes of the 2. to 4. twice to the susceper treated by metal contamination of known concentration in the 1, as to each metal component. The variation was obtained as: variation={(maximum value−minimum value)/average value}×100/2. Variations shown in Tables 2 and 3 are also values calculated in the same way.

TABLE 1

| | Mixed acid | | Metal to be quantitatively analyzed | | | | | |
|---|---|---|---|---|---|---|---|---|
| | | | Na | Al | Cr | Fe | Ni | Cu |
| Comparative Example | HF/$HNO_3$ | Recovery rate (1)/% | 72 | 78 | 71 | 74 | 73 | 70 |
| | | Recovery rate (2)/% | 91 | 93 | 86 | 87 | 87 | 86 |
| | | Average recovery rate/% | 82 | 86 | 79 | 81 | 80 | 78 |
| | | Variation | 11.656442 | 8.771930 | 9.554140 | 8.074534 | 8.750000 | 10.256410 |
| Comparative Example | HF/HCl/$H_2O_2$ | Recovery rate (1)/% | 100 | 96 | 96 | 99 | 92 | 94 |
| | | Recovery rate (2)/% | 90 | 85 | 80 | 82 | 84 | 83 |
| | | Average recovery rate/% | 95 | 91 | 88 | 91 | 88 | 89 |
| | | Variation | 5.263158 | 6.077348 | 9.090909 | 9.392265 | 4.545455 | 6.214689 |
| Example | HF/HCl/$HNO_3$ | Recovery rate (1)/% | 97 | 95 | 91 | 98 | 97 | 98 |
| | | Recovery rate (2)/% | 95 | 93 | 93 | 95 | 96 | 96 |
| | | Average recovery rate/% | 96 | 94 | 92 | 97 | 97 | 97 |
| | | Variation | 1.041667 | 1.063830 | 1.086957 | 1.554404 | 0.518135 | 1.030928 |

| | Mixed acid | | Metal to be quantitatively analyzed | | | | |
|---|---|---|---|---|---|---|---|
| | | | Mo | W | Ti | Nb | Ta |
| Comparative Example | HF/$HNO_3$ | Recovery rate (1)/% | 56 | 42 | 73 | 63 | 57 |
| | | Recovery rate (2)/% | 65 | 50 | 99 | 80 | 78 |
| | | Average recovery rate/% | 61 | 46 | 86 | 72 | 68 |
| | | Variation | 7.438017 | 8.695652 | 15.116279 | 11.888112 | 15.555556 |
| Comparative Example | HF/HCl/$H_2O_2$ | Recovery rate (1)/% | 83 | 71 | 93 | 89 | 82 |
| | | Recovery rate (2)/% | 81 | 70 | 91 | 92 | 86 |
| | | Average recovery rate/% | 82 | 71 | 92 | 91 | 84 |
| | | Variation | 1.219512 | 0.709220 | 1.086957 | 1.657459 | 2.380952 |
| Example | HF/HCl/$HNO_3$ | Recovery rate (1)/% | 93 | 80 | 96 | 96 | 90 |
| | | Recovery rate (2)/% | 100 | 81 | 96 | 93 | 99 |
| | | Average recovery rate/% | 97 | 81 | 96 | 95 | 95 |
| | | Variation | 3.626943 | 0.621118 | 0.000000 | 1.587302 | 4.761905 |

5. Quantitative Analysis of Metal Components by ICP-MS (2)

Table 2 and 3 below show quantitative analysis results (recovery rates, average of recovery rates and variation) obtained by performing, with number of times shown in Table 2 and 3 below, a process of subjecting the susceptor treated by metal contamination of a known concentration in the same way as in the 1 to processes of the 2 to 4, as to various metal components shown in Table 2 and 3 below by the use of various kinds of mixed acids shown in Table 2 and 3 below. Mixed acids shown in Table 2 and 3 below are aqueous solutions containing acids shown in the Tables as acid components and containing each acid in concentration shown in the Tables.

TABLE 2

| Recovery liquid | Number of times | Recovery rate | | | | | |
|---|---|---|---|---|---|---|---|
| | | Na | Al | Cr | Fe | Ni | Cu |
| $HF:H_2O_2 = 2\%:2\%$ (Comparative Example) | 1 | 91% | 87% | 88% | 87% | 91% | 95% |
| | 2 | 96% | 98% | 88% | 94% | 99% | 91% |
| | 3 | 96% | 92% | 89% | 85% | 89% | 92% |
| | 4 | 98% | 97% | 99% | 96% | 99% | 92% |
| | 5 | 90% | 85% | 86% | 81% | 85% | 86% |
| | 6 | 90% | 92% | 80% | 87% | 87% | 72% |
| | 7 | 92% | 89% | 87% | 89% | 92% | 93% |
| | 8 | 78% | 87% | 75% | 86% | 78% | 83% |
| | 9 | 100% | 96% | 98% | 97% | 96% | 98% |
| | 10 | 96% | 94% | 85% | 88% | 94% | 91% |
| | Average | 93% | 92% | 88% | 89% | 91% | 89% |
| | Variation | 11.81025 | 7.523192 | 13.43561 | 9.212123 | 11.79414 | 14.65606 |
| $HF:H_2O_2 = 18\%:18\%$ (Comparative Example) | 1 | 91% | 95% | 93% | 95% | 87% | 97% |
| | 2 | 99% | 95% | 90% | 91% | 92% | 92% |
| | 3 | 94% | 100% | 91% | 85% | 87% | 86% |
| | 4 | 93% | 99% | 91% | 87% | 92% | 84% |
| | Average | 94% | 97% | 91% | 89% | 90% | 90% |
| | Variation | 4.230685 | 2.386234 | 1.817159 | 5.558101 | 2.974665 | 7.018923 |
| $HCl:H_2O_2 = 2\%:2\%$ (Comparative Example) | 1 | 73% | 68% | 63% | 64% | 70% | 64% |
| | 2 | 90% | 89% | 83% | 76% | 84% | 86% |
| | Average | 81% | 79% | 73% | 70% | 77% | 75% |
| | Variation | 10.70643 | 13.37999 | 13.53577 | 9.206073 | 9.408594 | 14.8169 |
| $HF:HNO_3 = 2\%:2\%$ (Comparative Example) | 1 | 72% | 78% | 71% | 74% | 73% | 70% |
| | 2 | 91% | 93% | 86% | 87% | 87% | 86% |
| | Average | 82% | 86% | 79% | 80% | 80% | 78% |
| | Variation | 11.85557 | 8.317268 | 9.536486 | 8.099624 | 8.590793 | 10.31672 |
| $HF:HNO_3 = 2\%:63\%$ (Comparative Example) | 1 | 97% | 97% | 93% | 94% | 89% | 87% |
| | 2 | 95% | 73% | 91% | 92% | 83% | 64% |
| | 3 | 72% | 72% | 69% | 76% | 68% | 58% |
| | 4 | 89% | 77% | 91% | 90% | 83% | 57% |
| | Average | 88% | 80% | 86% | 88% | 81% | 66% |
| | Variation | 14.43056 | 15.86977 | 13.96839 | 9.845738 | 13.03433 | 22.52942 |
| $HCl:HNO_3 = 15\%:17\%$ (Comparative Example) | 1 | 88% | 96% | 89% | 92% | 90% | 74% |
| | 2 | 83% | 100% | 86% | 87% | 92% | 87% |
| | Average | 86% | 98% | 87% | 90% | 91% | 81% |
| | Variation | 2.783534 | 2.162472 | 1.668322 | 2.50828 | 1.231021 | 8.365455 |
| $HCl:HNO_3 = 5\%:51\%$ (Comparative Example) | 1 | 67% | 75% | 70% | 68% | 44% | 74% |
| | 2 | 86% | 95% | 85% | 81% | 57% | 93% |
| | Average | 76% | 85% | 77% | 75% | 51% | 83% |
| | Variation | 12.87928 | 11.91481 | 9.661576 | 8.57539 | 11.91922 | 11.63275 |
| $HF:HCl:H_2O_2 = 4\%/3\%/3\%$ (Comparative Example) | 1 | 99% | 83% | 94% | 99% | 99% | 98% |
| | 2 | 99% | 88% | 96% | 99% | 92% | 94% |
| | 3 | 98% | 85% | 81% | 92% | 96% | 94% |
| | 4 | 90% | 85% | 80% | 82% | 84% | 83% |
| | Average | 97% | 85% | 88% | 93% | 93% | 92% |
| | Variation | 4.843423 | 2.607979 | 9.477608 | 9.237332 | 8.028521 | 8.296885 |

| Recovery liquid | Number of times | Recovery rate | | | | |
|---|---|---|---|---|---|---|
| | | Mo | W | Ti | Nb | Ta |
| $HF:H_2O_2 = 2\%:2\%$ (Comparative Example) | 1 | 69% | 52% | 93% | 74% | 95% |
| | 2 | 76% | 48% | 98% | 74% | 98% |
| | 3 | 60% | 40% | 92% | 72% | 83% |
| | 4 | 69% | 37% | 97% | 67% | 86% |
| | 5 | 59% | 39% | 94% | 71% | 87% |
| | 6 | 64% | 34% | 98% | 80% | 71% |
| | 7 | 53% | 35% | 90% | 63% | 86% |
| | 8 | 71% | 42% | 89% | 69% | 91% |
| | 9 | 61% | 41% | 96% | 75% | 93% |
| | 10 | 65% | 47% | 98% | 61% | 83% |
| | Average | 65% | 42% | 94% | 71% | 87% |
| | Variation | 17.92586 | 21.62347 | 4.503831 | 13.48665 | 15.4867 |
| $HF:H_2O_2 = 18\%:18\%$ (Comparative Example) | 1 | 94% | 76% | 99% | 95% | 93% |
| | 2 | 85% | 61% | 95% | 87% | 95% |
| | 3 | 77% | 67% | 99% | 80% | 92% |

TABLE 2-continued

| | | | | | | |
|---|---|---|---|---|---|---|
| | | 4 | 84% | 69% | 96% | 91% | 96% |
| | | Average | 85% | 69% | 97% | 88% | 94% |
| | | Variation | 10.42471 | 11.02422 | 2.185086 | 8.171128 | 1.62415 |
| HCl:$H_2O_2$ = 2%:2% | 1 | 52% | 25% | 83% | 64% | 44% |
| (Comparative Example) | 2 | 50% | 25% | 85% | 62% | 43% |
| | Average | 51% | 25% | 84% | 63% | 43% |
| | Variation | 1.804632 | 0.19425 | 1.331291 | 2.139104 | 1.322807 |
| HF:$HNO_3$ = 2%:2% | 1 | 56% | 42% | 73% | 63% | 57% |
| (Comparative Example) | 2 | 65% | 50% | 99% | 80% | 75% |
| | Average | 61% | 46% | 86% | 72% | 67% |
| | Variation | 7.393014 | 8.732303 | 15.37552 | 11.40898 | 15.42041 |
| HF:$HNO_3$ = 2%:63% | 1 | 76% | 57% | 93% | 83% | 90% |
| (Comparative Example) | 2 | 87% | 65% | 94% | 93% | 90% |
| | 3 | 72% | 57% | 80% | 75% | 89% |
| | 4 | 81% | 61% | 98% | 93% | 93% |
| | Average | 79% | 60% | 91% | 86% | 91% |
| | Variation | 8.913299 | 6.491822 | 9.760876 | 10.52831 | 2.478012 |
| HCl:$HNO_3$ = 15%:17% | 1 | 70% | 49% | 29% | 29% | 42% |
| (Comparative Example) | 2 | 55% | 43% | 20% | 20% | 46% |
| | Average | 62% | 46% | 24% | 24% | 44% |
| | Variation | 11.84759 | 6.957114 | 19.04637 | 19.02423 | 3.910303 |
| HCl:$HNO_3$ = 5%:51% | 1 | 61% | 38% | 29% | 28% | 27% |
| (Comparative Example) | 2 | 72% | 52% | 23% | 25% | 32% |
| | Average | 67% | 45% | 26% | 27% | 30% |
| | Variation | 8.664072 | 15.01884 | 11.82173 | 6.452176 | 7.511449 |
| HF:HCl:$H_2O_2$ = 4%/3%/3% | 1 | 84% | 70% | 93% | 89% | 93% |
| (Comparative Example) | 2 | 73% | 76% | 93% | 74% | 82% |
| | 3 | 88% | 69% | 94% | 92% | 83% |
| | 4 | 61% | 60% | 81% | 72% | 86% |
| | Average | 77% | 69% | 90% | 81% | 86% |
| | Variation | 17.31926 | 11.6246 | 7.422523 | 12.15215 | 6.368361 |

TABLE 3

| Recovery liquid | Number of times | Recovery rate | | | | | | |
|---|---|---|---|---|---|---|---|---|
| | | Na | Al | Cr | Fe | Ni | Cu | Mo |
| HF:HCl:$HNO_3$ = | 1 | 95% | 91% | 99% | 93% | 99% | 97% | 95% |
| 8%/12%/14% | 2 | 98% | 94% | 99% | 99% | 99% | 92% | 89% |
| (Example) | 3 | 95% | 100% | 95% | 96% | 96% | 91% | 83% |
| | 4 | 99% | 93% | 98% | 98% | 93% | 91% | 87% |
| | 5 | 97% | 90% | 91% | 98% | 90% | 91% | 93% |
| | 6 | 92% | 91% | 96% | 99% | 97% | 95% | 94% |
| | 7 | 93% | 94% | 99% | 94% | 98% | 92% | 83% |
| | 8 | 99% | 99% | 98% | 93% | 91% | 96% | 85% |
| | 9 | 95% | 93% | 93% | 95% | 92% | 91% | 89% |
| | 10 | 99% | 100% | 95% | 96% | 91% | 92% | 93% |
| | Average | 96% | 94% | 96% | 96% | 95% | 93% | 89% |
| | Variation | 3.738757 | 4.984849 | 4.094723 | 3.11877 | 4.647783 | 3.209129 | 6.955777 |

| Recovery liquid | Number of times | Recovery rate | | | |
|---|---|---|---|---|---|
| | | W | Ti | Nb | Ta |
| HF:HCl:$HNO_3$ = | 1 | 84% | 93% | 94% | 100% |
| 8%/12%/14% | 2 | 80% | 91% | 83% | 92% |
| (Example) | 3 | 73% | 95% | 87% | 91% |
| | 4 | 78% | 94% | 90% | 97% |
| | 5 | 80% | 90% | 86% | 90% |
| | 6 | 84% | 91% | 99% | 96% |
| | 7 | 75% | 99% | 84% | 98% |
| | 8 | 77% | 97% | 97% | 92% |
| | 9 | 78% | 98% | 93% | 99% |
| | 10 | 76% | 96% | 94% | 96% |
| | Average | 78% | 94% | 91% | 95% |
| | Variation | 7.181595 | 5.022953 | 8.640351 | 4.794561 |

| Recovery liquid | Number of times | Recovery rate | | | | | |
|---|---|---|---|---|---|---|---|
| | | Li | Mg | K | Ca | V | Mn |
| HF:HCl:$HNO_3$ = | 1 | 92% | 96% | 94% | 95% | 100% | 96% |
| 8%/12%/14% | 2 | 89% | 94% | 88% | 100% | 99% | 93% |
| (Example) | 3 | 88% | 93% | 89% | 95% | 99% | 94% |
| | 4 | 87% | 91% | 87% | 97% | 93% | 92% |
| | 5 | 97% | 98% | 95% | 99% | 97% | 98% |

TABLE 3-continued

| | | | | | | |
|---|---|---|---|---|---|---|
| 6 | 95% | 98% | 97% | 93% | 92% | 100% |
| 7 | 94% | 100% | 93% | 85% | 98% | 99% |
| 8 | 97% | 96% | 97% | 86% | 99% | 100% |
| 9 | 99% | 91% | 94% | 93% | 100% | 95% |
| 10 | 99% | 95% | 96% | 94% | 99% | 95% |
| Average | 94% | 95% | 93% | 93% | 99% | 96% |
| Variation | 6.682799 | 4.522123 | 5.368057 | 7.763752 | 8.806553 | 3.823727 |

| Recovery liquid | Number of times | Recovery rate | | | | | |
|---|---|---|---|---|---|---|---|
| | | Co | Zn | Sr | Ag | Ba | Pb |
| HF:HCl:HNO$_3$ = | 1 | 95% | 92% | 94% | 98% | 98% | 83% |
| 8%/12%/14% | 2 | 93% | 91% | 94% | 96% | 98% | 86% |
| (Example) | 3 | 95% | 93% | 95% | 93% | 100% | 89% |
| | 4 | 93% | 93% | 93% | 95% | 98% | 89% |
| | 5 | 97% | 80% | 92% | 94% | 94% | 96% |
| | 6 | 99% | 78% | 90% | 91% | 90% | 99% |
| | 7 | 94% | 90% | 91% | 98% | 94% | 92% |
| | 8 | 94% | 91% | 91% | 96% | 92% | 98% |
| | 9 | 100% | 95% | 95% | 95% | 97% | 92% |
| | 10 | 97% | 91% | 94% | 100% | 96% | 94% |
| | Average | 96% | 89% | 93% | 96% | 96% | 92% |
| | Variation | 3.6461 | 9.552607 | 2.703794 | 4.56831 | 4.956766 | 8.699784 |

From the comparison between Examples and Comparative Examples shown in Tables 1 to 3, it can be confirmed that, in Examples, various metals can be recovered at a higher recovery rate (various metals can be recovered at an average recovery rate exceeding 75%) and variation in measurement results is smaller (variation lower than 10% as to various metals) by the use of a mixed acid of hydrofluoric acid, hydrochloric acid and nitric acid as the recovery liquid, than in Comparative Examples.

In addition, ICP-MS used for quantitative analysis in Examples is an apparatus capable of performing high-sensitive quantitative analysis. With ICP-MS, even a slight metal contamination would be able to be detected and quantitatively analyzed.

From the above results, it can be confirmed that, in Examples, cleanliness of a silicon carbide-based member was able to be highly accurately analyzed.

The SRc (average peak height of roughness curved surface) and the SPc (average peak height of cross-section curved surface) of the silicon wafer-placing surface of the susceptor for which the evaluation was performed were measured at four positions. Measurement results are shown in Table 4 below.

TABLE 4

| | SRc (μm) | SPc (μm) |
|---|---|---|
| Measurement position 1 | 1.73 | 1.73 |
| Measurement position 2 | 6.71 | 6.71 |
| Measurement position 3 | 1.85 | 1.85 |
| Measurement position 4 | 2.74 | 2.74 |

An aspect of the present invention is useful in a field of manufacturing a silicon wafer.

The invention claimed is:

1. A method of evaluating cleanliness of a member having a silicon carbide surface, which comprises:
   bringing the silicon carbide surface into contact with a mixed acid of hydrofluoric acid, hydrochloric acid and nitric acid;
   concentrating the mixed acid brought into contact with the silicon carbide surface by heating to obtain a concentrated liquid;
   adding a solution to the concentrated liquid to obtain a sample solution;
   performing quantitative analysis of metal components present in the sample solution by Inductively Coupled Plasma-Mass Spectrometry; and
   evaluating cleanliness of the member having the silicon carbide surface on the basis of a quantitative result of the metal components obtained by the quantitative analysis.

2. The method of evaluating cleanliness according to claim 1, wherein, in the mixed acid, a concentration of hydrofluoric acid ranges from 5 to 15 mass %, a concentration of hydrochloric acid ranges from 5 to 15 mass %, and a concentration of nitric acid ranges from 5 to 15 mass %.

3. The method of evaluating cleanliness according to claim 2, wherein the member having the silicon carbide surface is a member for manufacturing a silicon wafer.

4. The method of evaluating cleanliness according to claim 3, wherein the member for manufacturing the silicon wafer is a susceptor.

5. The method of evaluating cleanliness according to claim 1, wherein the solution added to the concentrated liquid is an aqueous solution of hydrofluoric acid and hydrogen peroxide.

6. The method of evaluating cleanliness according to claim 5, wherein the member having the silicon carbide surface is a member for manufacturing a silicon wafer.

7. The method of evaluating cleanliness according to claim 6, wherein the member for manufacturing the silicon wafer is a susceptor.

8. The method of evaluating cleanliness according to claim 1, wherein the member having the silicon carbide surface is a member for manufacturing a silicon wafer.

9. The method of evaluating cleanliness according to claim 8, wherein the member for manufacturing the silicon wafer is a susceptor.

* * * * *